US011284992B2

(12) United States Patent
Collins et al.

(10) Patent No.: US 11,284,992 B2
(45) Date of Patent: Mar. 29, 2022

(54) INTRAOCULAR LENS PLATFORM HAVING IMPROVED HAPTIC FORCE DISTRIBUTION

(71) Applicant: Alcon Inc., Fribourg (CH)

(72) Inventors: Stephen John Collins, Fort Worth, TX (US); Rakhi Jain, Fort Worth, TX (US); John Evan Radle, Flower Mound, TX (US); Jian Liu, Keller, TX (US); Michael Lee Mangum, Sunnyvale, CA (US)

(73) Assignee: Alcon, Inc., Fribourg (CH)

( * ) Notice: Subject to any disclaimer, the term of this patent is extended or adjusted under 35 U.S.C. 154(b) by 122 days.

(21) Appl. No.: 16/223,307

(22) Filed: Dec. 18, 2018

(65) Prior Publication Data

US 2019/0183632 A1 Jun. 20, 2019

Related U.S. Application Data

(60) Provisional application No. 62/607,004, filed on Dec. 18, 2017.

(51) Int. Cl.
*A61F 2/16* (2006.01)
*A61F 2/00* (2006.01)

(52) U.S. Cl.
CPC .............. *A61F 2/16* (2013.01); *A61F 2/0077* (2013.01); *A61F 2002/1681* (2013.01);
(Continued)

(58) Field of Classification Search
CPC .. A61F 2/16; A61F 2/0077; A61F 2002/1681; A61F 2002/1686; A61F 2002/1683; A61F 2250/0036
See application file for complete search history.

(56) References Cited

U.S. PATENT DOCUMENTS 4,704,123 A 11/1987 Smith
5,290,892 A 3/1994 Namdaran et al.
(Continued)

FOREIGN PATENT DOCUMENTS

WO 97/20523 A1 6/1997

OTHER PUBLICATIONS

Bausch & Lomb, "enVista IOL," http://www.bausch.com/ecp/our-products/cataract-surgery/lens-systems/envista-iol, downloaded Jun. 18, 2019, 5 pages.
(Continued)

*Primary Examiner* — Jerrah Edwards
*Assistant Examiner* — Tiffany P Shipmon
(74) *Attorney, Agent, or Firm* — Patterson & Sheridan, LLP

(57) ABSTRACT

An ophthalmic lens includes an optic comprising an anterior surface, a posterior surface, and an optic edge extending between the anterior surface and the posterior surface, the optic having an optical axis. The ophthalmic lens further includes a plurality of haptics extending from a periphery of the optic, each of the plurality of haptics including a gusset region, a distal region, and an elbow region connecting the gusset region to the distal region. The gusset region of each of the plurality of haptics extends from the periphery of the optic and spans a portion of the periphery of the optic. In addition, the gusset region of each of the plurality of haptics monotonically increases in thickness with increased distance from the periphery of the optic, while the distal region of each of the plurality of haptics monotonically decreases in thickness with increased distance from the elbow region.

20 Claims, 4 Drawing Sheets

(52) U.S. Cl.
CPC ............... *A61F 2002/1683* (2013.01); *A61F 2002/1686* (2013.01); *A61F 2250/0036* (2013.01)

(56) References Cited

U.S. PATENT DOCUMENTS

| | | | |
|---|---|---|---|
| 5,693,095 | A | 12/1997 | Freeman et al. |
| 5,716,403 | A * | 2/1998 | Tran .................. A61F 2/16 623/6.46 |
| 6,190,410 | B1 | 2/2001 | Lamielle et al. |
| 6,200,344 | B1 | 3/2001 | Lamielle et al. |
| 6,228,115 | B1 * | 5/2001 | Hoffmann ............. A61F 2/1616 623/6.49 |
| 6,398,809 | B1 * | 6/2002 | Hoffmann ............. A61F 2/1602 623/6.49 |
| 6,468,306 | B1 * | 10/2002 | Paul .................... A61F 2/1613 623/6.16 |
| 8,449,610 | B2 | 5/2013 | Laredo et al. |
| 8,758,435 | B2 | 6/2014 | Doraiswamy et al. |
| 8,969,429 | B2 | 3/2015 | Laredo et al. |
| 2003/0055499 | A1 | 3/2003 | Nguyen et al. |
| 2005/0125056 | A1 | 6/2005 | Deacon et al. |
| 2005/0187621 | A1 * | 8/2005 | Brady ................. A61F 2/1616 623/6.16 |
| 2011/0130833 | A1 * | 6/2011 | Scott .................. A61F 2/16 623/6.49 |
| 2016/0331520 | A1 | 11/2016 | Beer |

OTHER PUBLICATIONS

Taiwan Intellectual Property Office, Official Letter, Application No. 107145482, dated Nov. 11, 2019, 7 pages.

\* cited by examiner

INTRAOCULAR LENS PLATFORM HAVING IMPROVED HAPTIC FORCE DISTRIBUTION

CROSS-REFERENCE TO RELATED APPLICATIONS

This application claims the priority benefit of U.S. Provisional Patent Application No. 62/607,004, filed Dec. 18, 2017, the disclosure of which is incorporated herein by reference.

FIELD

The present disclosure relates generally to ophthalmic lenses and, more particularly, to an intraocular lens platform having improved haptic force distribution.

BACKGROUND

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraIntraocular lenses (IOLs)

An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During the surgical procedure, the surgeon may implant the selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each contacts the capsular bag, retaining the IOL in place.

Although existing IOLs may function acceptably well in many patients, they also have certain shortcomings. For example, existing IOL designs may include haptics that cause striae, or folds, in the posterior capsular bag. Such striae may result from the haptics having a relatively small angle of contact with the capsular bag, which may cause uneven force distribution around the periphery of the capsular bag. Because striae may negatively impact patient outcomes (e.g., by resulting in increased posterior capsular opacification (PCO) by providing a mechanism for the growth and/or migration of cells), haptic designs that reduce striae are desirable. Moreover, such designs should also have a volume and foldability conducive to maintaining acceptably small incision sizes as larger incisions may adversely affect the patient's recovery.

Accordingly, what is needed is an IOL having a haptic design that reduces striae (thereby addressing one cause of PCO) without negatively impacting rotational or axial stability or significantly complicating implantation.

SUMMARY

In certain embodiments, an ophthalmic lens includes an optic comprising an anterior surface, a posterior surface, and an optic edge extending between the anterior surface and the posterior surface, the optic having an optical axis. The ophthalmic lens further includes a plurality of haptics extending from a periphery of the optic, each of the plurality of haptics including a gusset region, a distal region, and an elbow region connecting the gusset region to the distal region. The gusset region of each of the plurality of haptics extends from the periphery of the optic and spans a portion of the periphery of the optic. In addition, the gusset region of each of the plurality of haptics monotonically increases in thickness with increased distance from the periphery of the optic, while the distal region of each of the plurality of haptics monotonically decreases in thickness with increased distance from the elbow region.

In certain embodiments, the present disclosure may provide one or more technical advantages. For example, the IOL platform described herein may increase the uniformity of haptic force distribution, thereby reducing posterior capsular folds (striae) while maintaining axial stability and rotational stability in majority of capsular bag sizes. More particularly, the IOL platform described herein may increase the uniformity of haptic force distribution by providing a greater angle of contact (greater than 50 degrees in some embodiments) as compared to current single piece IOLs (which may have angle of contacts ranging from 40-45 degrees).

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's disclosure in any way.

DETAILED DESCRIPTION

In general, the present disclosure relates to ophthalmic lenses (e.g., IOLs) that are rotationally and axially stable and that reduce the incidence of posterior capsule striae. More particularly, the present disclosure provides an ophthalmic lens includes an optic comprising an anterior surface, a posterior surface, and an optic edge extending between the anterior surface and the posterior surface, the optic having an optical axis. The ophthalmic lens further includes a plurality of haptics extending from a periphery of the optic, each of the plurality of haptics including a gusset region, a distal region, and an elbow region connecting the gusset region to the distal region. The gusset region of each of the plurality of haptics extends from the periphery of the optic and spans a portion of the periphery of the optic. In addition, the gusset region of each of the plurality of haptics monotonically increases in thickness with increased distance from the periphery of the optic, while the distal region of each of the plurality of haptics monotonically decreases in thickness with increased distance from the elbow region.

Figure 1:
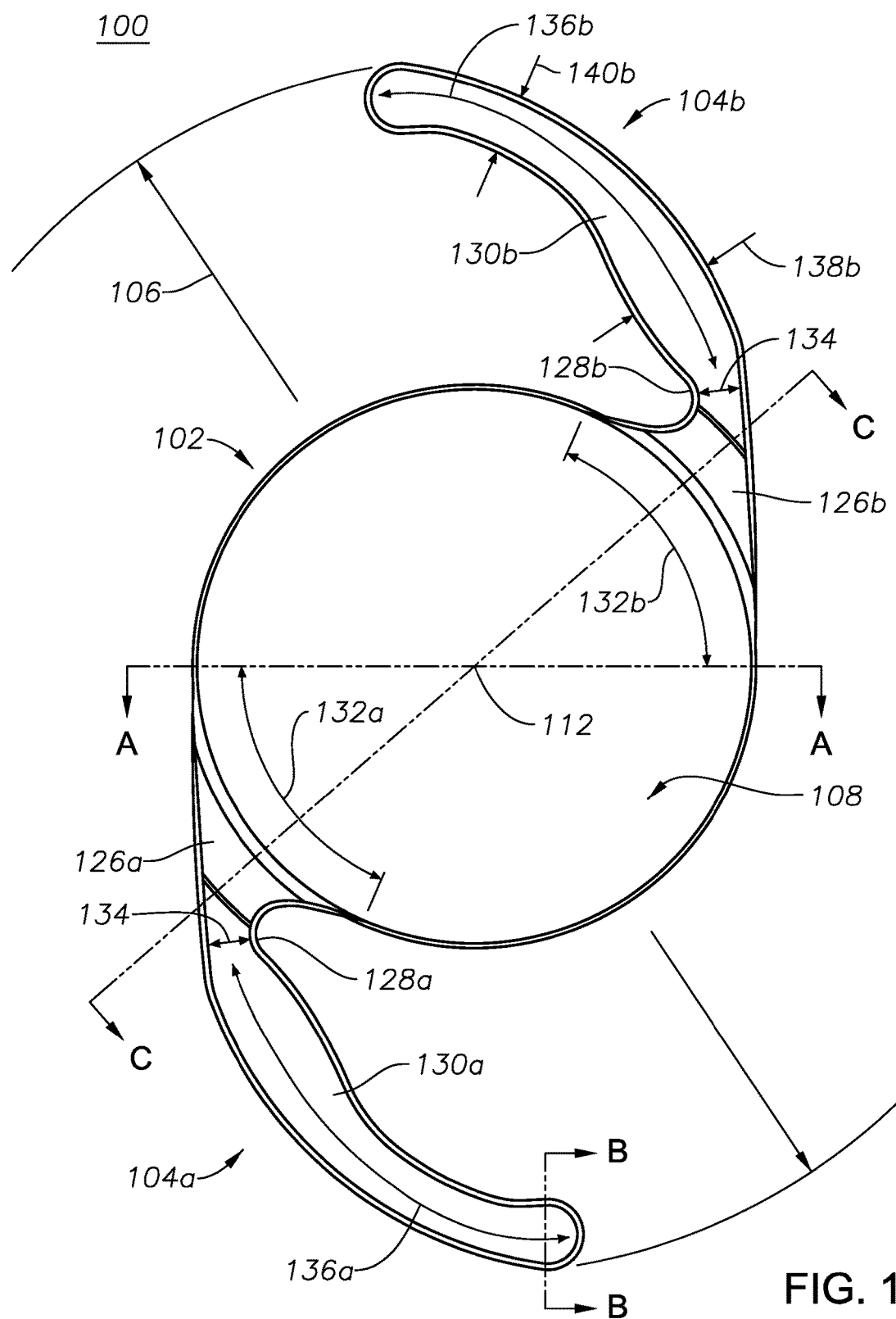
FIG. 1 illustrates a top view of an exemplary ophthalmic lens, according to certain embodiments of the present disclosure.
Figure 2:
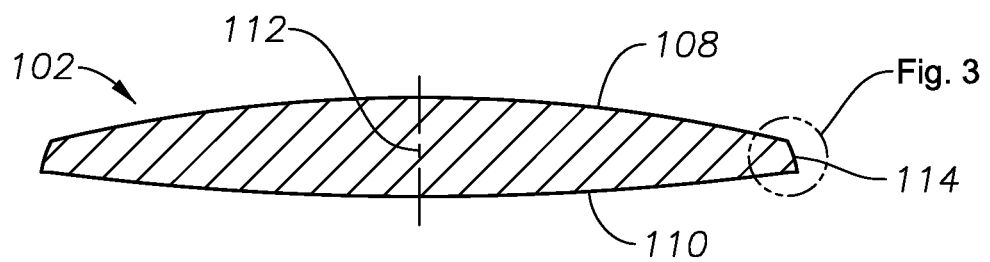
FIG. 2 illustrates a cross-sectional view of the optic of the exemplary ophthalmic lens depicted in FIG. 1 (along line A-A of FIG. 1)
Figure 3:
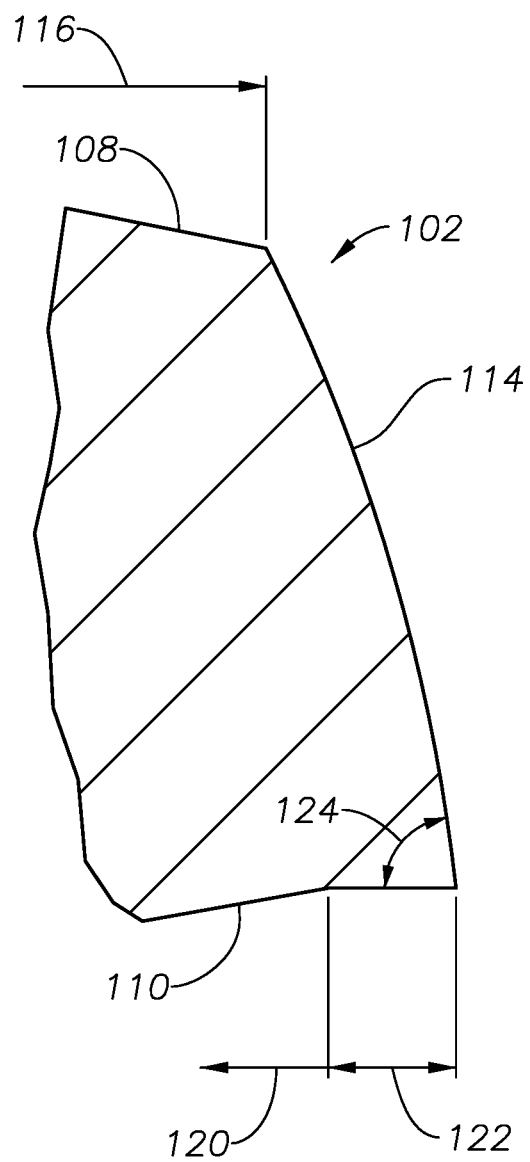
FIG. 3 illustrates a detailed view of the optic edge of the exemplary ophthalmic lens depicted in FIG. 1.
Figure 4:
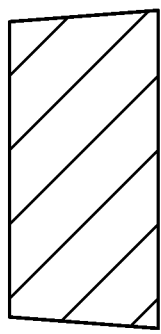
FIG. 4 illustrates a cross-sectional view of a haptic of the exemplary ophthalmic lens depicted in FIG. 1 (along line B-B of FIG. 1)
Figure 5:
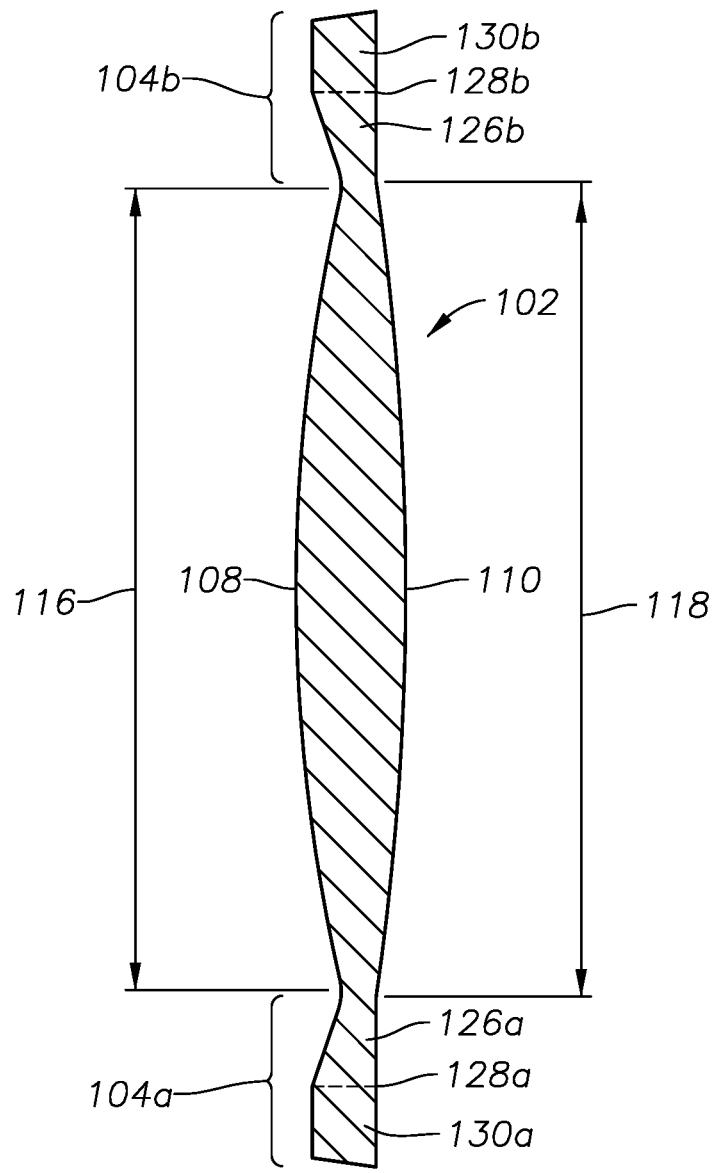
FIG. 5 illustrates a cross-sectional of the optic and haptics of the exemplary ophthalmic lens depicted in FIG. 1 (along line C-C of FIG. 1)
Figure 6:
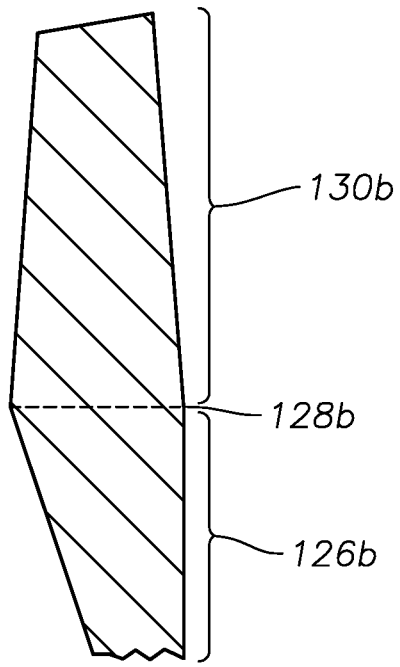
FIG. 6 illustrates a detailed cross-sectional view of the haptic of the exemplary ophthalmic lens depicted in FIG. 1.
Figure 7:
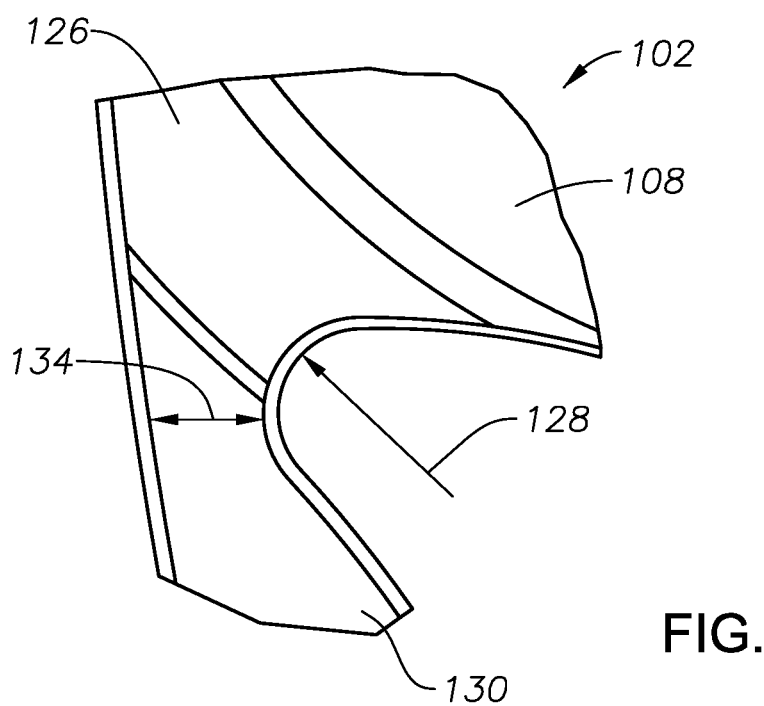
FIG. 7 illustrates a detailed view of the gusset region of the exemplary ophthalmic lens depicted in FIG. 1.

FIGS. 1-7 illustrate various views of an ophthalmic lens 100 (referred to below as IOL 100), according to certain embodiments of the present disclosure. IOL 100 may include an optic 102 and a plurality of haptics 104. In particular, FIG. 1 illustrates a top view of IOL 100, FIG. 2 illustrates a cross-sectional view of an optic 102 of 100 (along line A-A of FIG. 1), FIG. 3 illustrates a detailed view of an optic edge 114 of IOL 100, FIG. 4 illustrates a cross-sectional view of a haptic 104 of IOL 100 (along line B-B of FIG. 1), FIG. 5 illustrates a cross-sectional view of the optic 102 and haptics 104 of IOL 100 (along line C-C of FIG. 1), FIG. 6 illustrates a detailed cross-sectional view of the haptic 104 of IOL 100, and FIG. 7 illustrates a detailed view of a gusset region 126 of IOL 100.

IOL 100 may have an overall diameter 106 between 10 mm and 15 mm. In certain embodiments, overall diameter 106 may be approximately 13.5 mm. Although FIG. 1 depicts an IOL 100 having two haptics 104 (104a and 104b) defining the overall diameter 106, the present disclosure contemplates that IOL 100 may have any suitable number of haptics.

Optic 102 may include an anterior surface 108, a posterior surface 110, an optical axis 112, and an optic edge 114. Anterior surface and/or posterior surface may include any suitable surface profiles for correcting a patient's vision. For example, anterior surface and/or posterior surface 108 may be spheric, aspheric, toric, refractive, diffractive, or any suitable combination thereof. In other words, optic 102 may be one or more of a spheric lens, an aspheric lens, a toric lens, a multifocal lens (refractive or diffractive), an extended depth of focus lens, or any other suitable type of lens.

Anterior surface 108 may have an anterior surface diameter 116 between 4.5 mm and 7.0 mm. In one specific embodiment, anterior surface diameter 116 may be approximately 6 mm. Additionally, anterior surface 108 may comprise a full surface optic, meaning that the optic portion of anterior surface 108 extends to the optic edge 114. Alternatively, anterior surface 108 may include one or more transition regions (not depicted) between an edge of the optic region of anterior surface 108 and the optic edge 114.

Posterior surface 110 may have a posterior surface diameter 118 between 4.5 mm and 7.0 mm. In one specific embodiment, posterior surface diameter 118 may be approximately 6.15 mm (or may vary, depending on lens power, within a range including 6.15 mm). Additionally, posterior surface 108 may comprise an optic portion 120 and a transition portion 122 located between optic region 120 and optic edge 114 (as best depicted in FIG. 3). Alternatively, posterior surface 110 may comprise a full surface optic, meaning that the optic portion of posterior surface 110 extends to the optic edge 114.

In embodiments in which posterior surface 108 comprises an optic portion 120 and a transition portion 122 and the posterior surface diameter 118 is approximately 6.15 mm, optic portion 120 of posterior surface 110 may have a diameter of approximately 6 mm. Transition portion 122 may comprise one or more curved surfaces, one or more flat surfaces, or any suitable combination thereof. In certain embodiments, the intersection of transition portion 122 and optic edge 114 may form an angle 124 of near 90 degrees.

Optic edge 114 may extend between anterior surface 108 and posterior surface 110 and may comprise one or more curved surfaces, one or more flat surfaces, or any suitable combination thereof. In one specific embodiment, optic edge 114 may comprise a continuously curved surface extending between anterior surface 108 and posterior surface 110. In such embodiments, the continuously curved surface may not include any tangents parallel to optical axis 112, which may advantageously reduce the incidence of positive dysphotopsia results, at least in part, from edge glare.

Haptics 104 may each include a gusset region 126, an elbow region 128, and a distal region 130. Gusset region 126 may extend from the periphery of the optic 102 and may span angle 132 of the periphery of optic 102. In certain embodiments, angle 132 may be greater than or equal to 50 degrees. In certain other embodiments, angle 132 may be greater than or equal to 60 degrees. In other embodiment, angle 132 may be greater than or equal to 70 degrees. In one specific embodiment, angle 132 may be approximately equal to 70 degrees.

In certain embodiments, the overall thickness of each gusset region 126 may monotonically increase with increased distance from the optic axis 112 (as best depicted in FIGS. 5-6). In other words, each gusset region 126 may have a minimum thickness at the point of connection to the periphery of the optic 102, and the thickness may monotonically increase between the periphery of the optic 102 and the elbow region 128. For example, gusset region 126 may have a minimum thickness at the periphery of the optic between 0.16 mm and 0.40 mm. As another example, gusset region 126 may have a minimum thickness at the periphery of the optic between 0.20 mm and 0.35 mm. As another example, gusset region 126 may have a minimum thickness at the periphery of the optic of approximately 0.25 mm (for IOLs 100 having lower powers) and 0.35 mm (for IOLs 100 having higher powers).

In alternative embodiments, the overall thickness of each gusset region 126 may monotonically increase over only a portion of gusset region 126. Stated differently, gusset region 126 may monotonically increase in thickness over a first range of distances from the optic axis 112 and may have constant thickness or decreasing thickness (or a combination thereof) over a second range of distances from the optic axis 112.

Elbow region 128 may comprise a portion of the haptic 104 having the minimum width. For example, the width 134 of elbow region 128 may be between 0.40 mm and 0.65 mm. As another example, the width 134 of elbow region 128 may be approximately 0.50 mm. As a result of elbow region 128 comprising a portion of the haptic 104 having the minimum width, elbow region 128 may create a hinge allowing haptic 104 to flex while minimizing buckling and vaulting of optic 102.

Distal region 130 may extend from elbow region 128 and may have a length 136 in the range of 6 mm to 7.5 mm. In certain embodiments, distal region 130 may have a length 136 in the range of 6.5 mm to 7 mm. In one particular embodiment, distal region 130 may have a length 136 of approximately 6.8 mm.

In certain embodiments, distal region 130 varies in width along its length 136. In one particular embodiment, distal region 130 may have a maximum width 138 or approximately 0.90 mm and a minimum width 140 of approximately 0.65 mm. Additionally, the width of distal region 130 may vary between the posterior surface of the haptic 104 and the anterior surface of the haptic 104. For example, as illustrated in FIG. 4, the posterior surface of the haptic 105 may be wider than the anterior surfaces, in which case the above discussed widths refer to the width at the wider posterior surface. Although both the anterior and posterior surfaces of haptic 104 are depicted in FIG. 4 as being substantially flat, the present disclosure contemplates that, in certain embodiments, one or both of the anterior and posterior surfaces of haptic 104 may include a curvature. In such embodiments, the surface area of a haptic(s) 104 contacting the optic 102 or one another when the IOL 100 is folded for delivery may be reduced, thereby reducing the incidence of the haptic(s) 104 sticking to the optic 102 or one another after deliver. As a result, unfolding performance may be improved.

In certain embodiments, the overall thickness of each distal region 130 may monotonically decrease with increased distance from the elbow region 128. In other words, the thickness of the distal region 130 of each haptic 104 may monotonically decrease along its length 136. For example, distal region 130 may have a maximum thickness adjacent elbow region 128 between 0.33 mm and 0.57 mm. As another example, distal region 130 may have a maximum thickness adjacent elbow region 128 between 0.37 mm and 0.53 mm. As another example, distal region 130 may have a maximum thickness adjacent elbow region 128 of approximately 0.47 mm. From the point of maximum thickness, distal region 130 may have a linear decrease in thickness as a function of increased distance from the optical axis 112 (resulting in a non-linear decrease in thickness along the length 136 of distal region 130). As one particular example, the thickness of distal region 130 may decrease such that, in cross-section (see FIG. 5), the anterior surface of distal region 130 is sloped at an angle of approximately 3 degrees. Alternatively, from the point of maximum thickness, distal region 130 may have a non-linear decrease in thickness as a function of increased distance from the optical axis 112.

In alternative embodiments, the overall thickness of each distal region 130 may monotonically decrease over only a portion of distal region 130. Stated differently, distal region 130 may monotonically decrease in thickness over a first range of distances from the elbow region 128 and may have constant thickness or increasing thickness (or a combination thereof) over a second range of distances from the elbow region 128.

The above-described configuration of haptics 104 may provide one or more technical advantages. For example, the above-described configuration of haptics 104 may increase the uniformity of haptic force distribution, thereby reducing posterior capsular folds (striae) while maintaining axial stability and rotational stability in majority of capsular bag sizes. More particularly, the above-described configuration of haptics 104 may increase the uniformity of haptic force distribution by providing a greater angle of contact (greater than 50 degrees in some embodiments) as compared to current single piece IOLs (which may have angles of contacts ranging from 40-45 degrees). Moreover, the variation in thickness of the various regions of the haptics 104 may provide desired stability while minimizing volume, thereby facilitating smaller incision sizes.

In certain embodiments, all or a portion of the haptics 104 may have a textured surface. A textured haptic surface may reduce the incident of the haptics 104 sticking to the optic 102 during delivery. Additionally, the texturing on optic edge 114 may mitigate or minimize the edge glare by diffusing unwanted lights from edge reflection or transmission, thereby reducing the incidence of positive dysphotopsia.

A variety of techniques and materials can be employed to fabricate the above-described IOL 100. For example, the optic 102 of an IOL 100 can be formed of a variety of biocompatible polymeric materials. Some suitable biocompatible materials include, without limitation, soft acrylic polymeric materials, hydrogel materials, polymethymethacrylate, or polysulfone, or polystyrene-containing copolymeric materials, or other biocompatible materials. By way of example, in one embodiment, the optic 102 may be formed of a soft acrylic hydrophobic copolymer such as those described in U.S. Pat. Nos. 5,290,892; 5,693,095; 8,449,610; or 8,969,429. The haptics 104 of the IOLs 100 can also be formed of suitable biocompatible materials, such as those discussed above. While in some cases, the optic 102 and haptics 104 of an IOL can be fabricated as an integral unit, in other cases they can be formed separately and joined together utilizing techniques known in the art.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic lens, comprising:
   an optic comprising an anterior surface, a posterior surface, and an optic edge extending between the anterior surface and the posterior surface, the optic having an optical axis; and
   a plurality of haptics extending from a periphery of the optic, each of the plurality of haptics comprising a gusset region, a distal region, and an elbow region connecting the gusset region to the distal region, wherein:
   the gusset region of each of the plurality of haptics extends from the periphery of the optic and spans a portion of the periphery of the optic;
   the gusset region of each of the plurality of haptics monotonically increases in thickness with increased distance from the periphery of the optic; and
   the distal region of each of the plurality of haptics monotonically decreases in thickness with increased distance from the elbow region across the entire distal region, wherein the distal region of each of the plurality of haptics comprises an ending region of each haptic.

2. The ophthalmic lens of claim 1, wherein the portion of the periphery of the optic spanned by the gusset region of each of the plurality of haptics is at least sixty degrees of the periphery of the optic.

3. The ophthalmic lens of claim 1, wherein the portion of the periphery of the optic spanned by the gusset region of each of the plurality of haptics is at least approximately seventy degrees of the periphery of the optic.

4. The ophthalmic lens of claim 1, wherein the elbow region of each of the plurality of haptics comprises a region of each haptic having a minimum haptic width.

5. The ophthalmic lens of claim 1, wherein each of the plurality of haptics comprises an anterior haptic surface and a posterior haptic surface, wherein, for at least a portion of each of the plurality of haptics, a width of the posterior haptic surface is greater than a width of the anterior haptic surface, wherein the width of the anterior haptic surface and the width of the posterior haptic surface are defined in a direction perpendicular to the optical axis.

6. The ophthalmic lens of claim 1, wherein at least a portion of a surface of each of the plurality of haptics is textured.

7. The ophthalmic lens of claim 1, wherein:
the optic edge defines a surface having a single radius of curvature; and
the surface does not have any tangents parallel to the optical axis.

8. The ophthalmic lens of claim 1, wherein the distal region of each of the plurality of haptics linearly decreases in thickness with increased distance from the optical axis.

9. The ophthalmic lens of claim 1, wherein the distal region of each of the plurality of haptics non-linearly decreases in thickness with increased distance from the elbow region.

10. The ophthalmic lens of claim 1, wherein the gusset region of each of the plurality of haptics linearly increases in thickness with increased distance from the periphery of the optic.

11. The ophthalmic lens of claim 1, wherein the gusset region of each of the plurality of haptics non-linearly increases in thickness with increased distance from the periphery of the optic.

12. An ophthalmic lens, comprising: an optic comprising an anterior surface, a posterior surface, and an optic edge extending between the anterior surface and the posterior surface, the optic having an optical axis;
a plurality of haptics extending from a periphery of the optic, each of the plurality of haptics comprising a gusset region, a distal region, and an elbow region connecting the gusset region to the distal region, wherein:
each of the plurality of haptics comprises an anterior haptic surface and a posterior haptic surface, wherein, for at least a portion of each of the plurality of haptics, a width of the posterior haptic surface is greater than a width of the anterior haptic surface, wherein the width of the anterior haptic surface and the width of the posterior haptic surface are defined in a direction perpendicular to the optical axis;
the gusset region of each of the plurality of haptics extends from the periphery of the optic and spans at least seventy degrees of the periphery of the optic;
the gusset region of each of the plurality of haptics monotonically increases in thickness with increased distance from the periphery of the optic;
the elbow region of each of the plurality of haptics comprises a region of each haptic having a minimum haptic width;

the distal region of each of the plurality of haptics monotonically decreases in thickness with increased distance from the elbow region across the entire distal region, wherein the distal region of each of the plurality of haptics comprises an ending region of each haptic; and
at least a portion of a surface of each of the plurality of haptics is textured.

13. The ophthalmic lens of claim 12, wherein:
the optic edge defines an edge surface having a single radius of curvature; and
the edge surface does not have any tangents parallel to the optical axis.

14. The ophthalmic lens of claim 12, wherein the distal region of each of the plurality of haptics linearly decreases in thickness with increased distance from the optical axis.

15. The ophthalmic lens of claim 12, wherein the distal region of each of the plurality of haptics non-linearly decreases in thickness with increased distance from the elbow region.

16. The ophthalmic lens of claim 12, wherein the gusset region of each of the plurality of haptics linearly increases in thickness with increased distance from the periphery of the optic.

17. The ophthalmic lens of claim 12, wherein the gusset region of each of the plurality of haptics non-linearly increases in thickness with increased distance from the periphery of the optic.

18. An ophthalmic lens, comprising:
an optic comprising an anterior surface, a posterior surface, and an optic edge extending between the anterior surface and the posterior surface, the optic having an optical axis; and
a plurality of unfenestrated haptics extending from a periphery of the optic at a gusset region, each of the plurality of haptics comprising a gusset region, a distal region, and an elbow region connecting the gusset region to the distal region, wherein:
the gusset region of each of the plurality of haptics spans at least seventy degrees of the periphery of the optic;
the distal region of each of the plurality of haptics monotonically decreases in thickness with increased distance from the elbow region across the entire distal region, wherein the distal region of each of the plurality of haptics comprises an ending region of each haptic; and
at least a portion of a surface of each of the plurality of haptics is textured.

19. The ophthalmic lens of claim 18, wherein the optic edge defines an edge surface having a single radius of curvature and the edge surface does not have any tangents parallel to the optical axis.

20. The ophthalmic lens of claim 18, wherein each of the plurality of haptics comprises an anterior haptic surface and a posterior haptic surface, wherein, for at least a portion of each of the plurality of haptics, a width of the posterior haptic surface is greater than a width of the anterior haptic surface, wherein the width of the anterior haptic surface and the width of the posterior haptic surface are defined in a direction perpendicular to the optical axis.

* * * * *